(12) United States Patent
Tenkanen et al.

(10) Patent No.: US 6,593,113 B1
(45) Date of Patent: Jul. 15, 2003

(54) IN VITRO METHOD FOR PROVIDING TEMPLATES FOR DNA SEQUENCING

(75) Inventors: Tuomas Tenkanen, Espoo (FI); Timo Soininen, Espoo (FI); Harri Savilahti, Helsinki (FI); Kirsi Multanen, Helsinki (FI)

(73) Assignee: Finnzymes Oy, Espoo (FI)

( * ) Notice: Subject to any disclaimer, the term of this patent is extended or adjusted under 35 U.S.C. 154(b) by 0 days.

(21) Appl. No.: 09/462,013

(22) PCT Filed: Jul. 10, 1998

(86) PCT No.: PCT/FI98/00586

§ 371 (c)(1),
(2), (4) Date: Dec. 30, 1999

(87) PCT Pub. No.: WO99/04035

PCT Pub. Date: Jan. 28, 1999

(30) Foreign Application Priority Data

Jul. 14, 1997 (FI) .................................................. 972992

(51) Int. Cl.⁷ ........................... C12P 19/34; C12Q 1/68; C12N 15/64
(52) U.S. Cl. ......................... 435/91.1; 435/6; 435/91.2; 435/91.4
(58) Field of Search .......................... 435/6, 91.1, 91.2, 435/91.4, 375; 536/23.1, 24.1, 24.3, 24.31, 24.33, 24.5

(56) References Cited

FOREIGN PATENT DOCUMENTS

WO        9523875         9/1995

OTHER PUBLICATIONS

Krishnan et al, NAR 19(22):6177–6182, 1991.*
Strathmann et al, PNAS 88:1247–1250, Feb. 1991.*
Devine et al., NAR 22(18):3765–3772, 1994.*
Fischer et al, Gene 180: 81–89, 1996.*
Savilahti et al, EMBO 14(19):4893–4903, 1995.*

* cited by examiner

*Primary Examiner*—Sean McGarry
*Assistant Examiner*—M Schmidt
(74) *Attorney, Agent, or Firm*—Birch, Stewart, Kolasch & Birch, LLP

(57) ABSTRACT

The present invention relates to an in vitro method for providing unique templates for DNA sequencing and to a kit, which can be used, when employing the selection method of this invention. The examined DNA is subjected to a DNA transposition reaction and to an amplification reaction. The amplification reaction is carried out in the presence of a fixed primer and a selective primer having a complementary sequence to the end of a transposon DNA. A transposition reaction can be carried out also in the presence of a transposon or transposons, which have different ends enabling the design of selective primers for both ends. Each size of the amplification products represents one template for a sequencing reaction.

14 Claims, 15 Drawing Sheets

IN VITRO METHOD FOR PROVIDING TEMPLATES FOR DNA SEQUENCING

This application is the national phase under 35 U.S.C. §371 of PCT International Application No. PCT/FI98/00586 which has an International filing date of Jul. 10, 1998 which designated the United States of America.

The present invention relates to the sequencing of DNA and in particular to the selection of unique templates for DNA sequencing. The selection methods of this invention can be performed fully in vitro. The invention further relates to a kit which can be used when employing the selection method of this invention.

DNA sequencing is a widely used method which is indispensable within modem molecular biology. One factor limiting sequencing is the shortness of the sequence to be read using one primer. Present-day techniques make it possible to read about 1000 bases starting from the primer. In practice, the range to be read covers about 400 to 800 bases. When sequencing a long DNA the examined DNA has been divided up into smaller fragments and the fragments have been separately sequenced, or the so called "DNA walk" method has been used.

In addition, it is essential that only one template is used in a single sequencing reaction. In the known methods, the problem has been solved by transforming the sequencing vector comprising the examined DNA into a bacterial cell, usually into *Escherichia coli*, and by isolating single colonies from the culture plate.

1. In the "DNA walk" method, the examined DNA is inserted into a vector and the inserted DNA is sequenced as far as possible by a known primer located in the vector. Using the obtained sequence, a new primer is designed, on which the sequencing is further continued (Itakura et al 1984 and Sambrook et al, 1989). The method is repeated until the entire sequence under examination has been exposed. The method is time-consuming and costly. The result from the previous round is needed for the next round, and new unique primers are required for each round.
2. The dividing up of the DNA into smaller, overlapping fragments has been performed by a number of different methods:
   DNA mapping using restriction enzymes and subcloning of the restriction products into sequencing vectors (Sambrook et al, 1989);
   the so called "shot gun" sequencing method where the DNA is randomly divided up into fragments and cloned into sequencing vectors (Sulston et al, 1992), and
   the so called exodeletion method where the DNA under examination is ligated into a sequencing vector and shortened by means of an exonuclease (Sambrook et al, 1989 and Ausubel et al, 1989).

All of the above methods are laborious and in each one, the DNA must be transformed into a bacterium (usually into *E. coli*) so as to produce a unique DNA template to be sequenced.

Furthermore, various kinds of methods based on DNA transposition have been disclosed for sequencing DNA. The majority of these methods are based on in vivo transposition (U.S. Pat. No. 4,716,105 and Strathmann et al 1991). The only known sequencing method (U.S. Pat. No. 5,728,551) exploiting in vitro transposition is based on using Ty1 integrase activity and even here, only the transposition reaction is carried out in vitro; the transposition products are transformed into *Escherichia coli* so as to obtain single sequencing templates. Related art is disclosed also in the U.S. Pat. No. 4,683,202, U.S. Pat. No. 5,212,080, U.S. Pat. No. 5,645,991, and in Kasai et al (1992), Krishnan et al (1993), and Roach et al (1995).

It would be highly advantageous if the selection of single sequencing templates through a single cell culture step could be fully avoided. Even in the known, partly in vitro methods, the amplification products should be transformed into a bacterium and single colonies are to be picked in order to obtain unique templates for sequencing the DNA.

The present invention aims at eliminating the problems relating to the prior art and, therefore, it is an object of the present invention to provide a simple method for fragmenting larger DNA segments into pieces enabling the sequencing of whole segment by using one or a few sequencing primers.

It is another object of this invention to provide, fully in vitro, a unique sequencing template for a single DNA sequencing reaction.

According to one embodiment (later called embodiments A and B) of this invention the examined DNA is subjected to a DNA transposition reaction and to an amplification reaction. The amplification reaction is carried out in the presence of a first, fixed primer, hybridizing at a known position in the examined DNA or if the examined DNA is part of a vector for example, adjacent to the examined DNA, and a second, selective primer, hybridizing at the insertion site of a transposon. These reactions result in amplification products which can be separated on the basis of their size difference. By suitably selecting the amplification products, whose size difference is in the range of the reading capacity of the sequencing system used, normally in the range of 200 to 600 bp, overlapping DNA templates can be obtained for sequencing. The target DNA can range from a few base pairs up to 40 kilo base pairs. The only limiting factor for not choosing as target DNA even longer DNA segments is the inability of the present amplification reactions, such as PCR, to produce longer DNA segments.

According to another embodiment (later called embodiment C) of this invention a transposition reaction is carried out in the presence of the examined DNA and in the presence of a transposon or transposons which have different ends enabling the design of selective primers for both ends. The transposon ends can be part of the same molecule or separate molecules. The amplification reaction is carried out in the presence of the selective primers designed for both transposon ends. The amplification products are situated at random positions in the target DNA. To be able to cover the whole sequence of the target DNA, a sufficient number of the amplification products needs to be selected for sequencing. Very long DNA segments can be sequenced by selecting the templates according to this embodiment. The present-day amplification reactions, such as PCR, are not a limiting factor. One advantage is that no sequence data of the target DNA is needed, nor is any subcloning procedure necessary.

One object of this invention is to provide a kit which comprises a transposon recognizable by a transposase enzyme, the transposase enzyme, a fixed primer hybridizing at a known position in the examined DNA or if the examined DNA is part of a vector for example, adjacent to the examined DNA, and a selective primer including a sequence complementary to the transposon joining end.

One further object of this invention is to provide a kit which comprises a selective primer, a fixed primer, a transposon recognizable by a transposase enzyme, and the transposase enzyme, and wherein the transposon and the transposase enzyme are provided as a transposition complex.

One still further object of this invention is to provide a kit which comprises two different transposon ends recognizable by a transposase enzyme or transposase enzymes, the transposase enzyme or transposase enzymes, and selective primers including a sequence complementary to the transposon joining ends.

These and other objects, together with the advantages thereof over known sequencing methods and kits, which shall become apparent from the specification which follows, are accomplished by the invention as hereinafter described and claimed.

Figure 4:
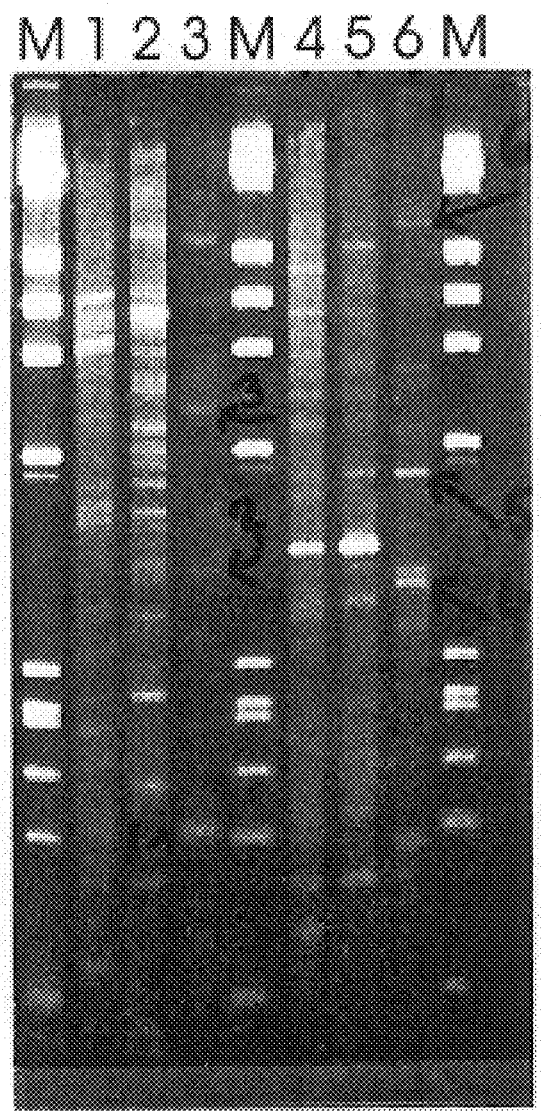

FIG. 4 shows the result of a selective PCR reaction on an agarose gel as described in Example 1. M=Lambda/HindIII+Phix174/HaeIII DNA marker (Finnzymes Oy, Espoo, Finland). The lane numbers correspond to the reaction numbers in Table 2.

Figure 5:
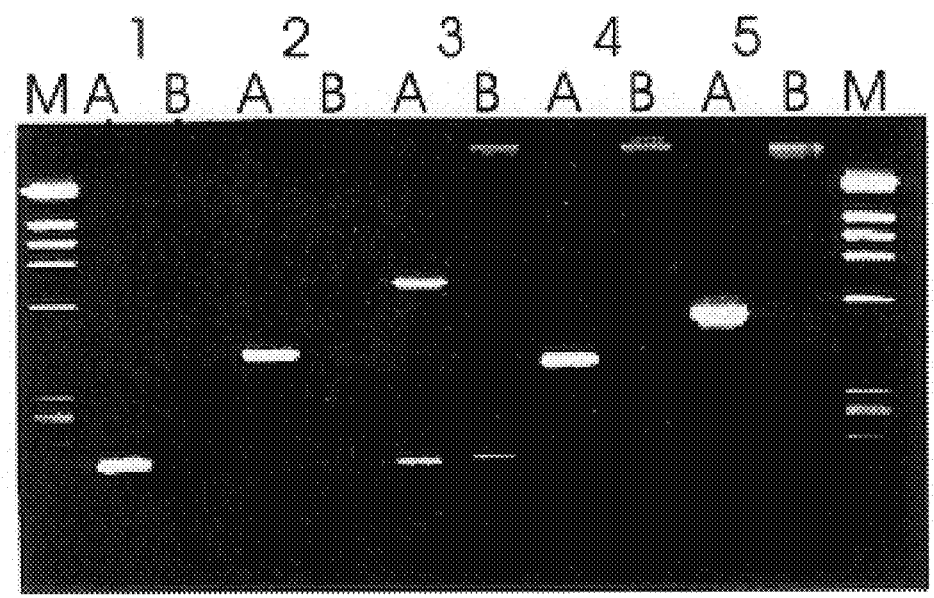

FIG. 5 shows the isolated DNA templates for sequencing on an agarose gel. M=Lambda/HindIII+Phix174/HaeIII DNA marker (Finnzymes Oy, Espoo, Finland). The lane numbers correspond to the fragment numbers marked by arrows in FIG. 4. Reaction A is performed by both primers, reaction B is performed by the selective primer only.

Figure 6:
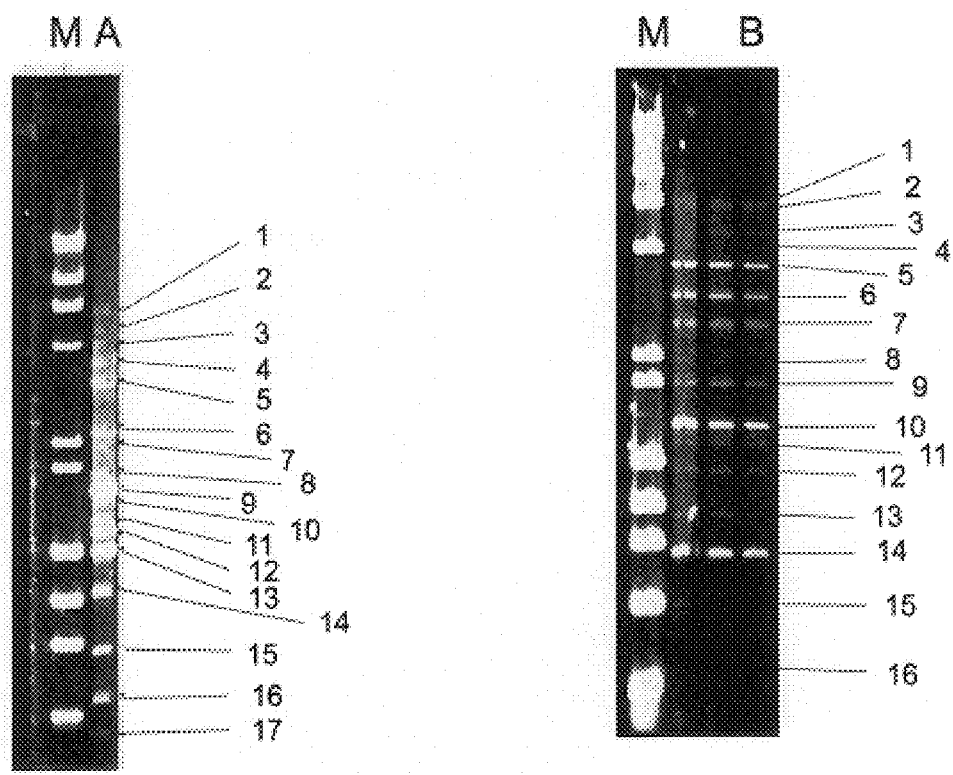

FIG. 6 shows the results of selective PCR reactions on an agarose gel as disclosed in Example 2. M=Lambda/HindIII+Phix174/HaeIII DNA marker (Finnzymes Oy, Espoo, Finland). "A" refer to the reaction A and "B" refer to reaction B. The numbers corresponds to the DNA fragments selected to the second PCR.

Figure 7A:
Figure 7B:
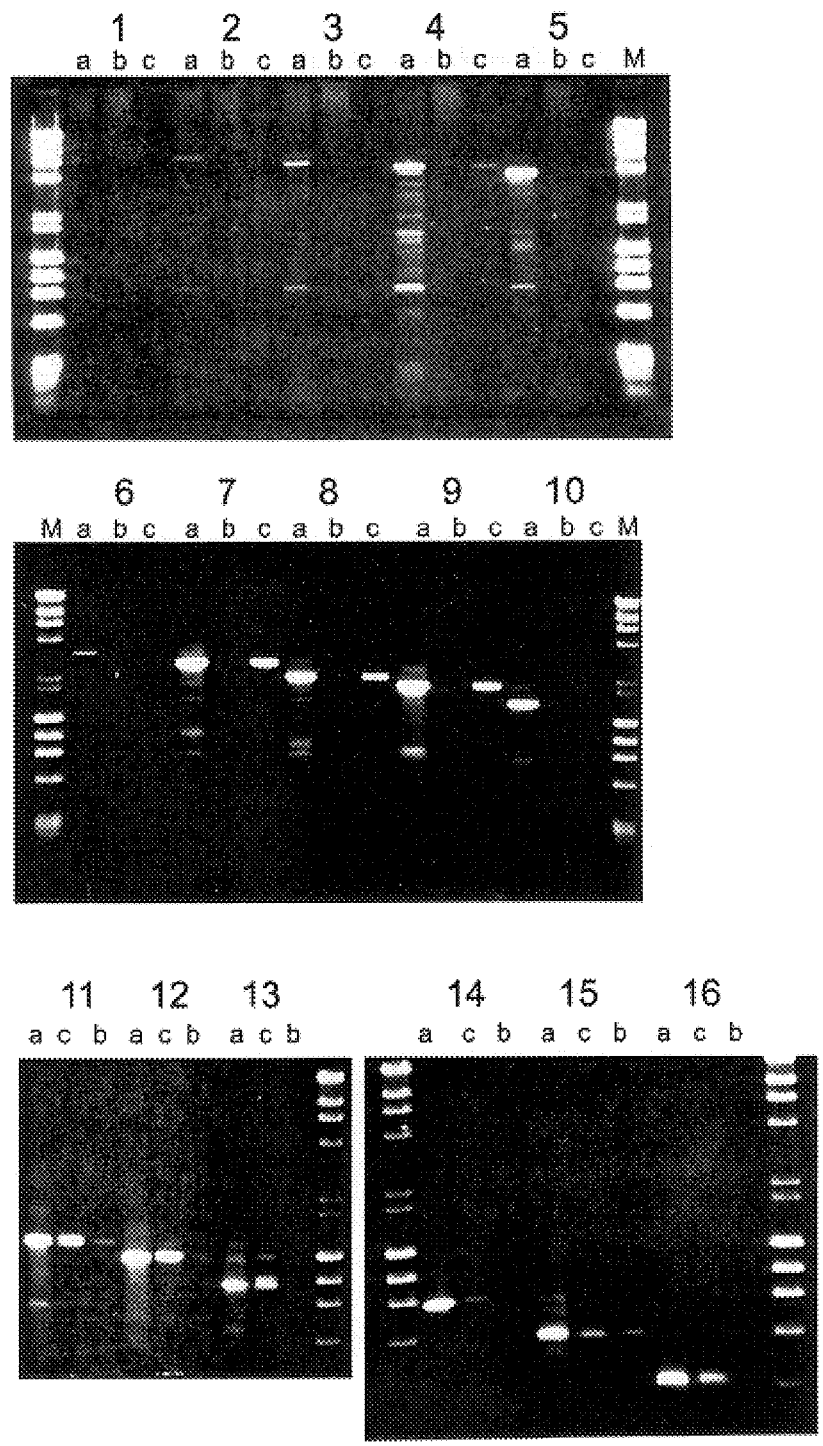

FIG. 7A shows the results of second PCR reactions on an agarose gel as disclosed in Example 2. M=Lambda/HindIII+Phix174/HaeIII DNA marker (Finnzymes Oy, Espoo, Finland). The lane numbers correspond to the fragment numbers marked in FIG. 6. In FIG. 7B a=reaction with both primers, b=reaction only with the fixed primer, c=reaction only with the selective primer.

Figure 8:
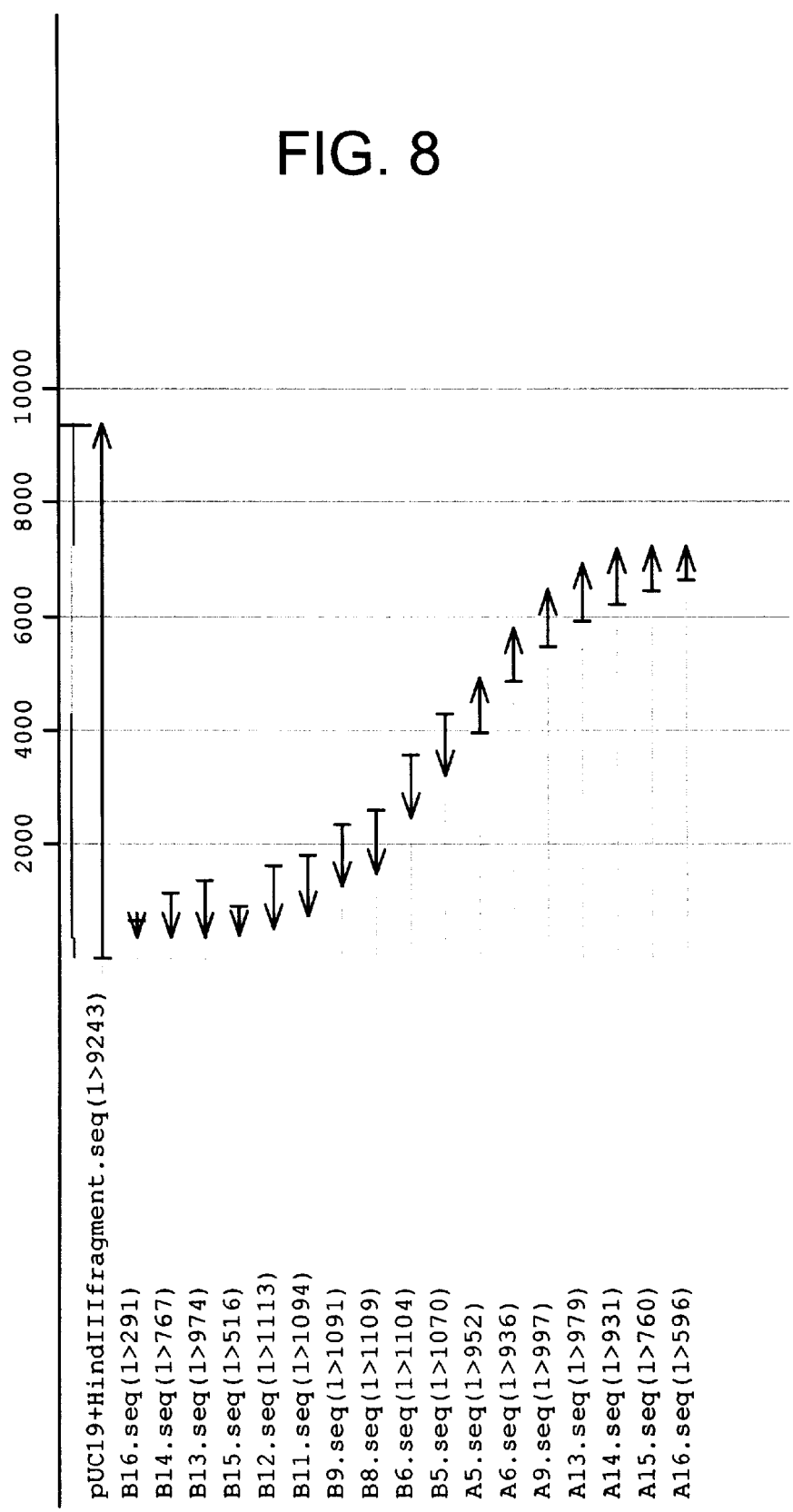

FIG. 8 shows the sequence assembly of the Example 2 results.

Figure 9:
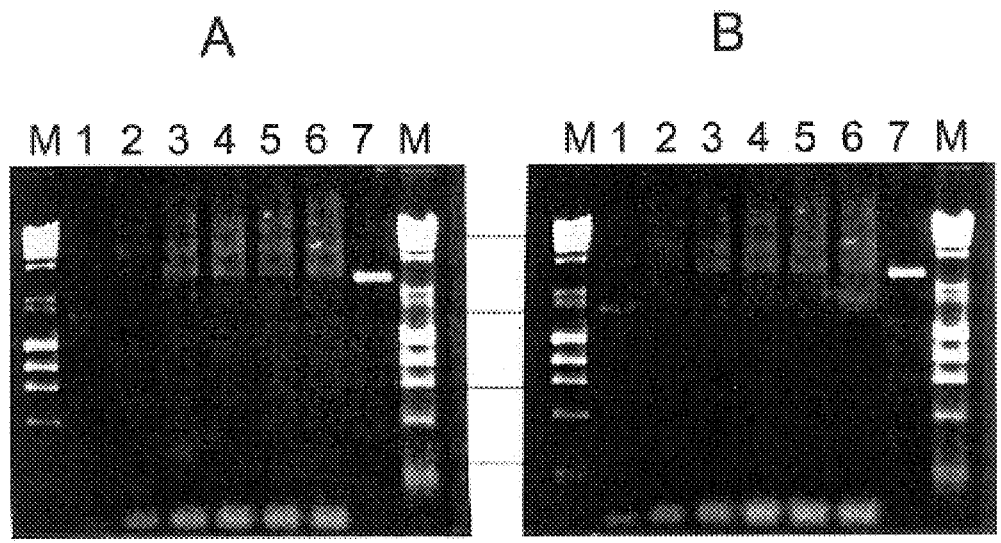

FIG. 9 shows the results of transposition reaction on an agarose gel as disclosed in Example 3. M=Lambda/HindIII+Phix174/HaeIII DNA marker (Finnzymes Oy, Espoo, Finland). Lane 1=transposition reaction without MuA transposase. Lanes 2 to 6=identical lanes each representing 10 μl samples of transposition reaction. Lane 7 represents linearized pUC19. A=gel before cutting off. B=gel after cutting off.

Figure 10:
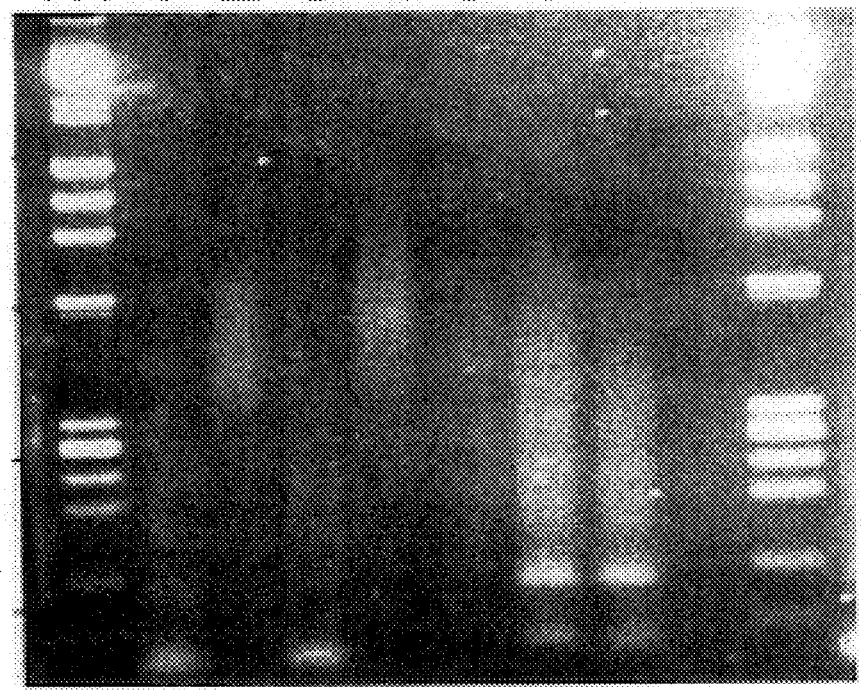

FIG. 10 shows the results of first PCR in Example 3. M=Lambda/HindIII+Phix174/HaeIII DNA marker (Finnzymes Oy, Espoo, Finland). The lane numbers correspond to the reaction numbers in Table 4.

Figure 11:
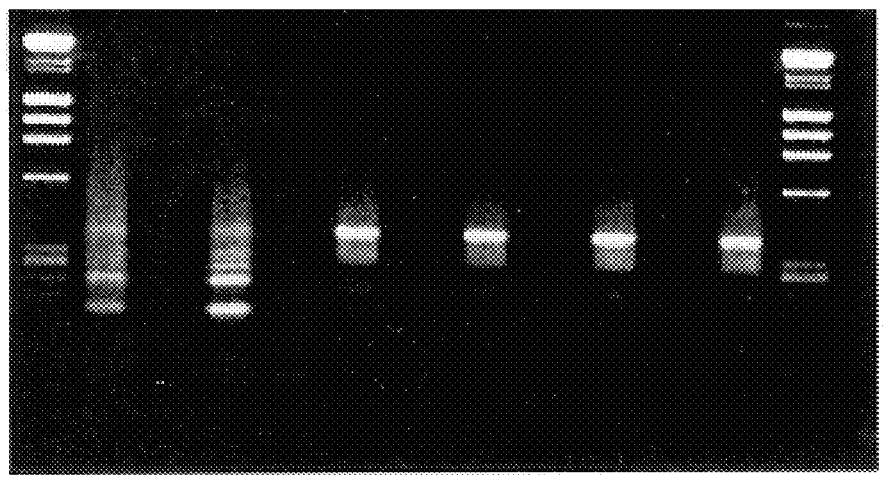
Figure 11:
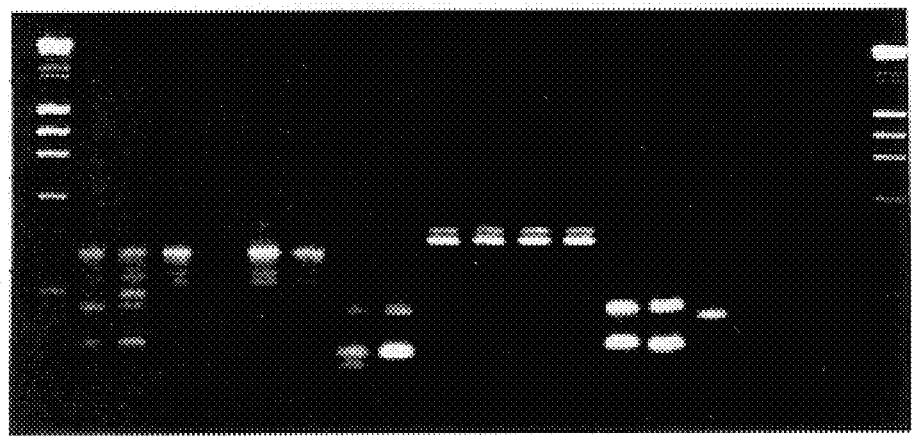

FIG. 11 shows the results of second selective PCR on a 2% agarose gel as disclosed in Example 3. M=Lambda/HindIII+Phix174/HaeIII DNA marker (Finnzymes Oy, Espoo, Finland). The lane numbers correspond to the reaction numbers in Table 5.

Figure 12:
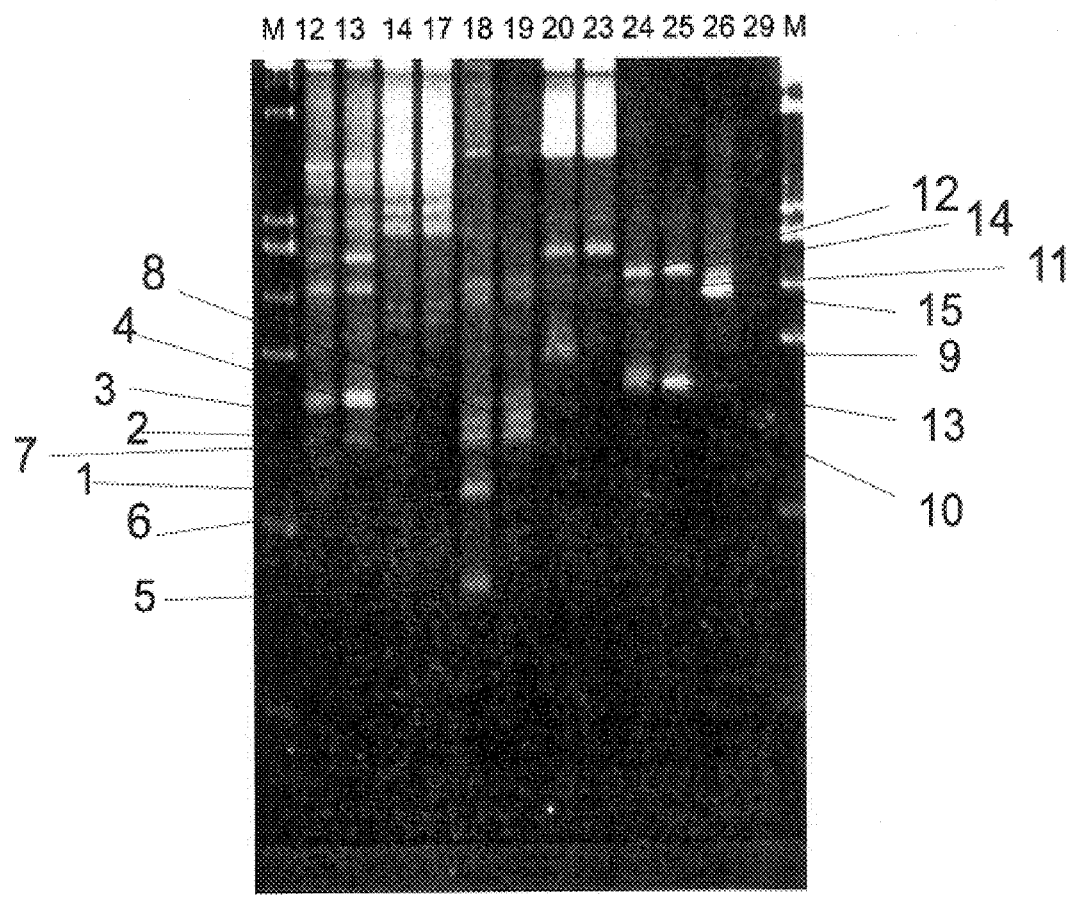

FIG. 12 shows the results of second selective PCR on a 4% Metaphor agarose (FMC) gel as disclosed in Example 3. M=Lambda/HindIII+Phix174/HaeIII DNA marker (Finnzymes Oy, Espoo, Finland). The lane numbers correspond to the reaction numbers in Table 5. The numbers at the side refer to the fragment numbers selected for the third PCR reaction.

Figure 13:
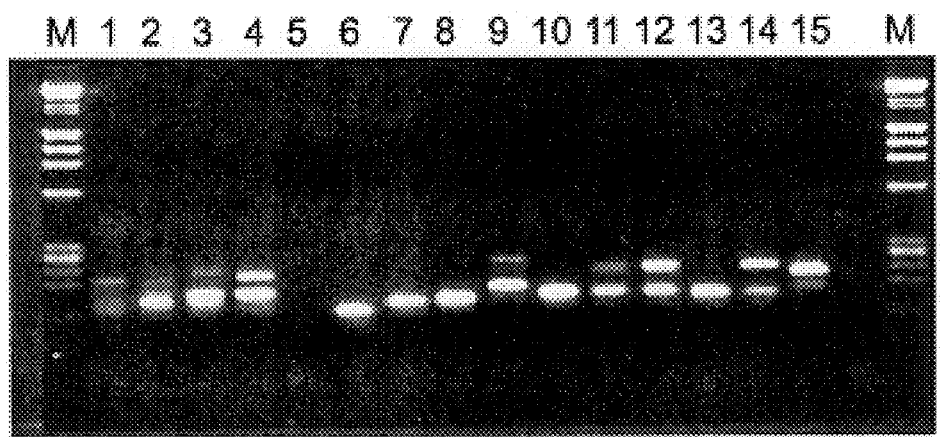

FIG. 13 shows the results of third PCR on an agarose gel as disclosed in Example 3. M=Lambda/HindIII+Phix174/HaeIII DNA marker (Finnzymes Oy, Espoo, Finland). The lane numbers refer to the reaction numbers in Table 6 and to the fragment numbers in FIG. 12.

Figure 14:
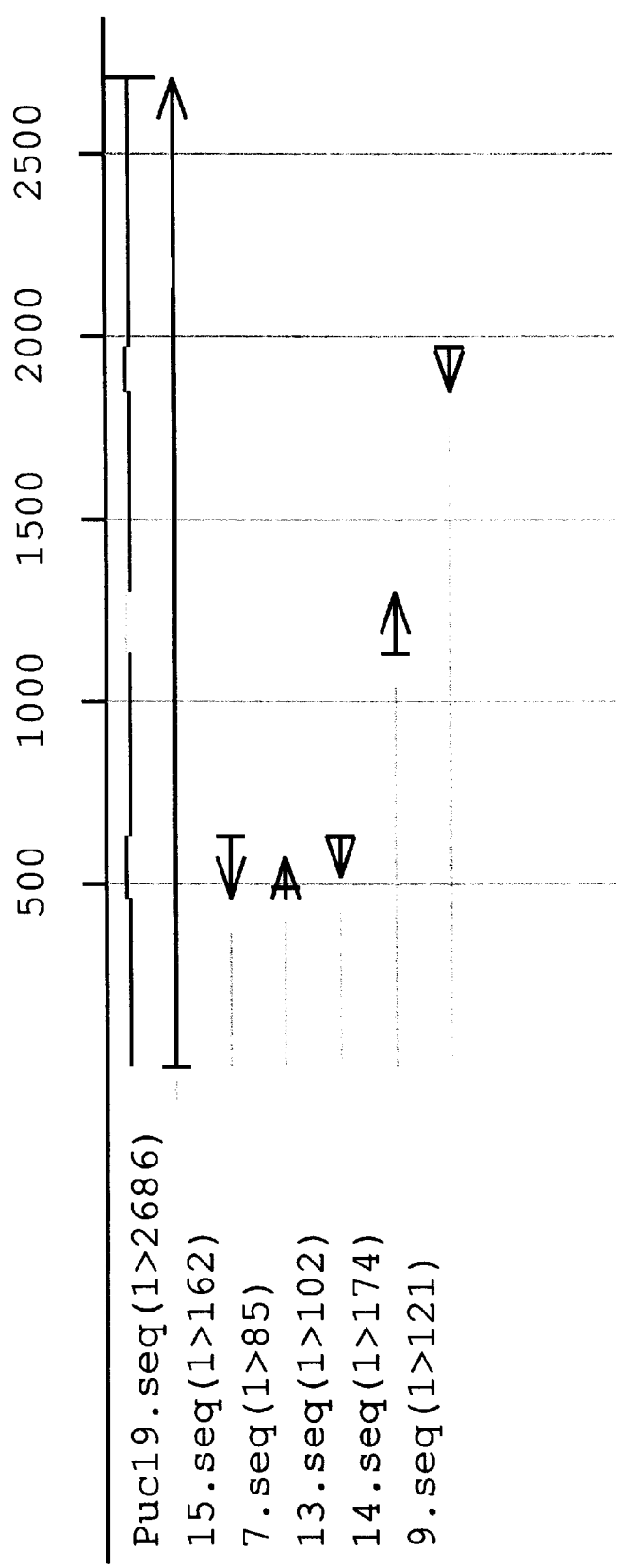

FIG. 14 shows the sequence assembly of the Example 3 results.

As explained above, this invention provides an in vitro method for selecting templates for DNA sequencing.

The term "DNA sequencing" refers to the determination of the sequence of purine and pyrimidine bases constituting a deoxyribonucleic acid segment. The purines commonly found in DNA are adenine (A) and guanine (G), the pyrimidines commonly found are cytosine (C) and thymine (T). A DNA sequence analysis results in a variation of the four bases designated as ATCGTGC etc.

Embodiment A

According to the first embodiment of this invention the method comprises the following steps:

a) A transposition reaction is carried out in the presence of a target DNA, which is a circular DNA or which is part of a circular DNA and in the presence of a transposon.

A "target DNA" is a segment of the DNA of interest to be fully or partially sequenced. The target DNA can range from a few base pairs up to 40 kilo base pairs. The limiting factor for not choosing as target DNA even longer DNA segments is the inability of the present amplification reactions, such as PCR, to produce longer DNA segments. However, in the third embodiment (C) of this invention, the PCR reaction is not a limiting factor and very long DNA segments can be sequenced according to that embodiment.

A "transposon" is a segment of DNA that can insert itself to a target DNA at random or at almost random locations. Transposons used in transposition reactions in vivo normally contain genes coding for enzymes, which are needed in a transposition reaction, but they also contain DNA which is not necessary for the transposition reaction. In reactions in vitro it is sufficient that the transposon used contains only the necessary DNA capable of forming a functional complex with a transposase or integrase enzyme and possibly even with other enzymes needed in a transposition reaction.

It has been shown by Savilahti et al (1995) that a functional transposition complex can be formed using only the ends of phage Mu transposon genome and MuA transposase enzyme.

The term "transposon" is intended to mean a DNA segment or segments which is/are recognizable by a transposase or an integrase enzyme and which is/are capable of forming a functional complex for a transposition reaction.

The term "transposase" is intended to mean an enzyme capable of forming a functional complex with a transposon or transposons needed in a transposition reaction including integrases from retrotransposons and retroviruses.

A "transposition reaction" is a reaction wherein a transposon inserts into a target DNA at random or at almost random sites. Essential components in a transposition reaction are a transposon and a transposase or an integrase enzyme or some other components needed to form a functional transposition complex. The method of this invention is exemplified by employing the transposition complex formed by the ends of Mu genome and MuA transposase enzyme (Savilahti et al., 1995). However, the transposition method is not critical for this invention. All transposition systems capable of inserting amplification primer sites in a random or in an almost random manner are useful in this invention (Craig, 1995). Examples of such systems are Ty1 (Devine and Boeke, 1994, and International Patent Application WO 95/23875), Transposon Tn7 (Craig, 1996), $Tn_{10}$ and IS10 (Kleckner et al. 1996), Mariner transposase (Lampe et al., 1996), Tc1 (Vos et al., 1996, 10(6), 755–61), Tn5 (Park .et al., 1992), P element (Kaufmnan and Rio, 1992) and Tn3 (Ichikawa and Ohtsubo, 1990), bacterial insertion sequences (Ohtsubo and Sekine, 1996), retroviruses (Varmus and Brown 1989) and retrotransposon of yeast (Boeke, 1989).

Due to the high sensitivity of the known amplification methods, such as PCR (U.S. Pat. No. 4,683,195, U.S. Pat. No. 4,683,202 and U.S. Pat. No. 4,965,188), the transposition reaction in this embodiment need not be very efficient. Preferably, transposons are inserted into the target DNA in conditions allowing insertion only into a fraction of target molecules to minimize the possibility of having the target DNA with two or more transposon inserts. In case amplification products have sites for selective primer at both ends they are unsuitable for use as sequencing templates.

The transposition reaction is preferably carried out by using a transposition complex comprising only the ends of a transposon DNA and a transposase enzyme resulting in a complete cleavage of the target DNA after the insertion of the transposon.

One transposon insertion linearizes the target DNA, whereas two or more insertions shorten the target DNA giving a smear below the linearized target DNA on an agarose gel. If 5% or less of the target DNA molecules become linearized, the result is sufficient but does not limit the subsequent selective amplification reactions.

b) The target DNA is amplified by using as amplification primers a first primer, the fixed primer, at a known location, and a second primer, the selective primer, at the transposon insertion site.

The "fixed primer" is intended to mean a DNA primer having a sequence complementary to the known sequence in the target DNA or if the target DNA is part of a vector, complementary to the known sequence in the vector adjacent to the insertion site of the target DNA. The vector may be any sequencing vector such as the vectors of the pUC series or their derivatives.

Figure 3:
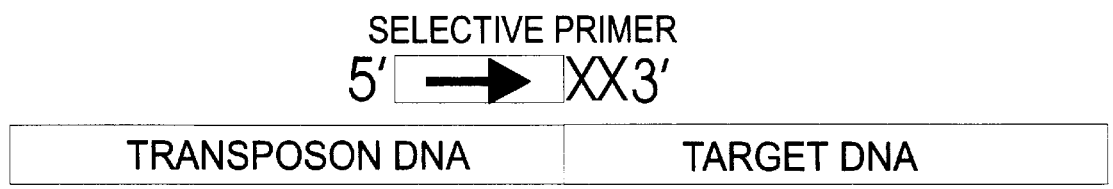
FIG. 3 illustrates the structure of a selective primer, wherein X=additional selective nucleotide.

The "selective primer" is intended to mean a primer having a sequence complementary to the joining end of the transposon DNA (complementary to that strand having 5' end at the joining). The selective primer is in 5'→3' direction towards the target DNA and has 0 to 10, preferably 0 to 5 additional nucleotides of known identity at its 3' end (FIG. 3).

The term "transposon joining end" means that end of the double stranded transposon DNA, which joins to the target DNA at the insertion site. The transposon joining end does not refer to the strand actually ligating to the target DNA. For example the 3' end of the transposon MuA joining end ligates to the 5' end of the target DNA leaving a gap between the 3' end of the target DNA and 5' end of transposon joining end.

A selective amplification reaction, such as PCR, is carried out by using the fixed primer and the selective primer as amplification primers. The additional known nucleotides at the 3' end of the selective primer cause selection of the amplification products. An increasing amount of additional nucleotides improves the selection. In the absence of any additional nucleotides at the 3' end of the selective primer, the amplification product is a mixture of products of varying sizes making the isolation of products of a specific size very difficult. This is because of the random nature of the transposition reaction in vitro. By adding one additional nucleotide to the 3' end of the selective primer, the number of possible templates can be decreased to one-fourth compared to a PCR reaction performed without selection. Two additional nucleotides decrease the amount of templates to one-sixteenth, three additional nucleotides to one-sixty-fourth, and so on. A similar approach can be found in Liang P. and Pardee B. (1992) in differential display of mRNA. However, no one has previously suggested the insertion of PCR primer sites to target DNA and the production of sequencing templates for PCR by using selective primers according to the principle disclosed here.

The use of selective primers in the amplification reaction results in specific amplification products varying in size, each size representing one template for a sequencing reaction.

It is preferable to minimize the unspecific PCR products in the selective PCR by performing a "Hot Start PCR". "Hot Start" can be done by any method known in the art including the addition of DNA polymerase to the reactions after a preheating of samples, isolation of template from DNA polymerase with a wax or using an inactive DNA polymerase that is activated by heat treatment (AmpliTaq Gold, Perking Elmer, USA). Specificity can also be increased by performing an additional PCR before the selective PCR using non selective primer pairs located just before the primers used in selective PCR and transferring small amount of that product into the selective PCR. The method is known as "nested PCR". Unspecific products can, however, also be used for sequencing if they represent only one DNA template.

To get large PCR products it is preferable to use DNA polymerase mixtures designed for long PCR. Such mixtures, however, often contain 3'–5' exonuclease activity also called proof reading activity that can cleave the selective nucleotides from the 3' ends of the selective primers. This problem can also occur if proof reading enzymes like "Vent" or "Deep Vent" from New England Biolabs, USA or Pfu DNA polymerase from Stratagene, USA are used. This phenomenon can be avoided by using phosphorothioate linkages on the last two 3' bases of the selective primers (De Noronha, C. M. C. and Mullins, J. I., 1992).

c) The amplification products are separated on the basis of their size by methods known in the art such as gel electrophoresis, capillary electrophoresis, HPLC or other well-known methods.

The specific amplification products varying in size are separated on the basis of their size difference by running them on an agarose gel for example, and by picking the separate "bands" into a new amplification reaction, such as PCR, by means of, e.g., a needle or a stick and performing a PCR using the same primers as in the selective amplification. Reaction products of different sizes are obtained, each size corresponding to a separate transposition reaction. The exact position of each PCR product is known in the studied DNA.

By suitably selecting PCR products whose size difference is in the range of the reading capacity of the used sequencing system, normally in the range of 200 to 600 bp, overlapping DNA templates are obtained for sequencing. By using the same fixed primer, it is even possible to sequence a larger DNA segment at one go.

One possible method for selecting suitable templates for sequencing is to use differently labeled fixed and selective primers and to test that both labels are present in the purified amplification product. The labels can be for example radioactive labels or fluorescent labels and the testing can be performed with an appropriate equipment depending on the labels. From the amplification products are selected for use as templates in sequencing those which have both labels.

d) The target DNA is sequenced by using as templates amplification products overlapping each other and varying in size from each other.

The sequencing method can be any sequencing method known in the prior art like the nucleotide specific chemical reaction and cleavage reactions of Maxam and Gilbert (1977) and the primer extension reactions in the presence of nucleotide specific terminators as disclosed by Sanger et al (1977) preferably by using the cycle sequencing method.

Embodiment B

According to a second embodiment of this invention the target DNA is a linear DNA or part of a linear DNA. A partial sequence of the target DNA or a DNA adjacent to the insertion site of the target DNA is known enabling the design of a fixed primer having a sequence complementary to the known partial sequence. Accordingly, the position of the fixed primer is known within the target DNA or within the linear DNA comprising the target DNA.

The embodiment B comprises the same method steps as the embodiment A except that there is no linearization step of the target DNA as in the embodiment A.

Embodiment C

Figure 1:
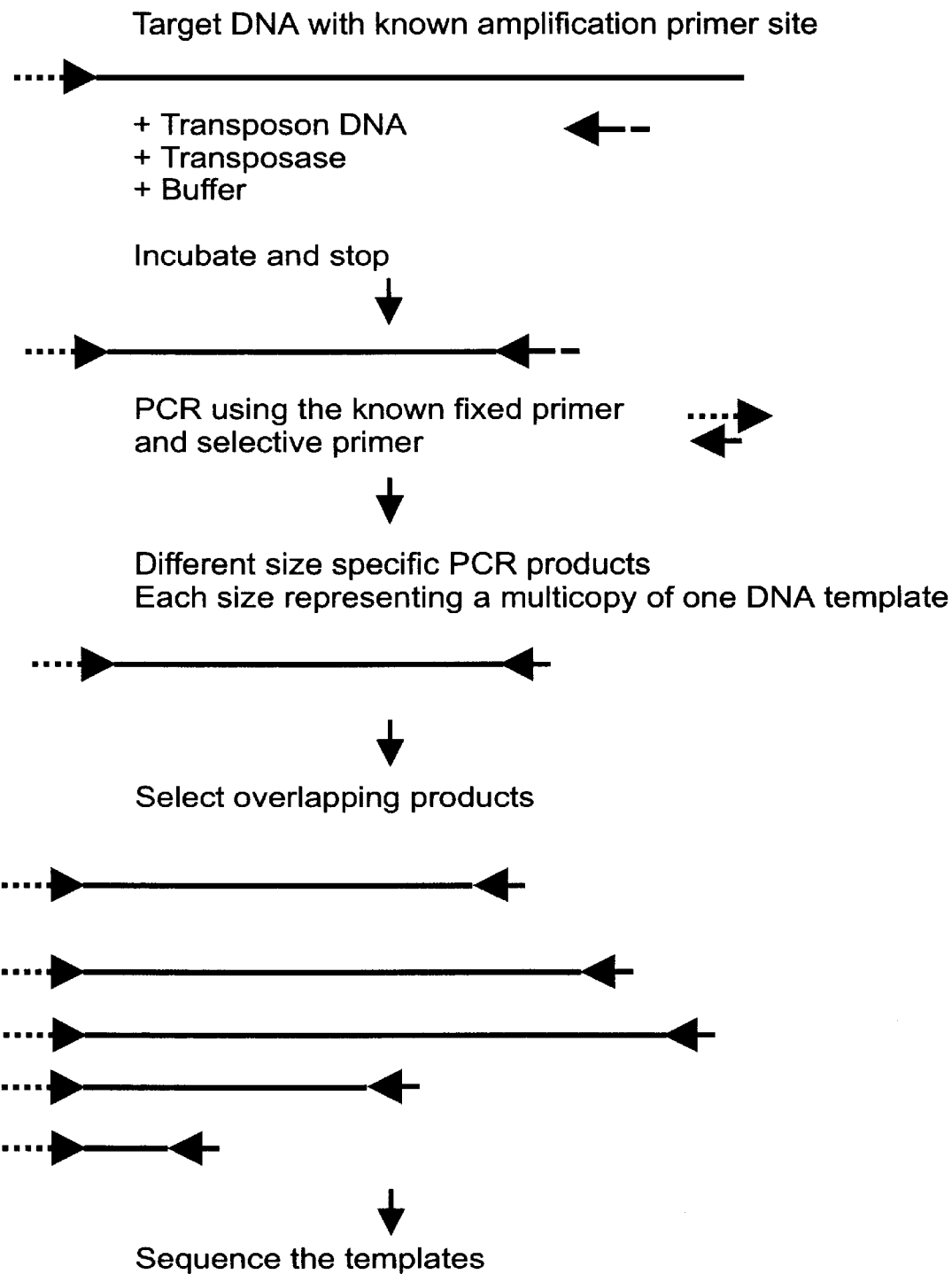
FIG. 1 is a schematic representation of the principle of first (A) and second (B) embodiments of the invention.
Figure 2:
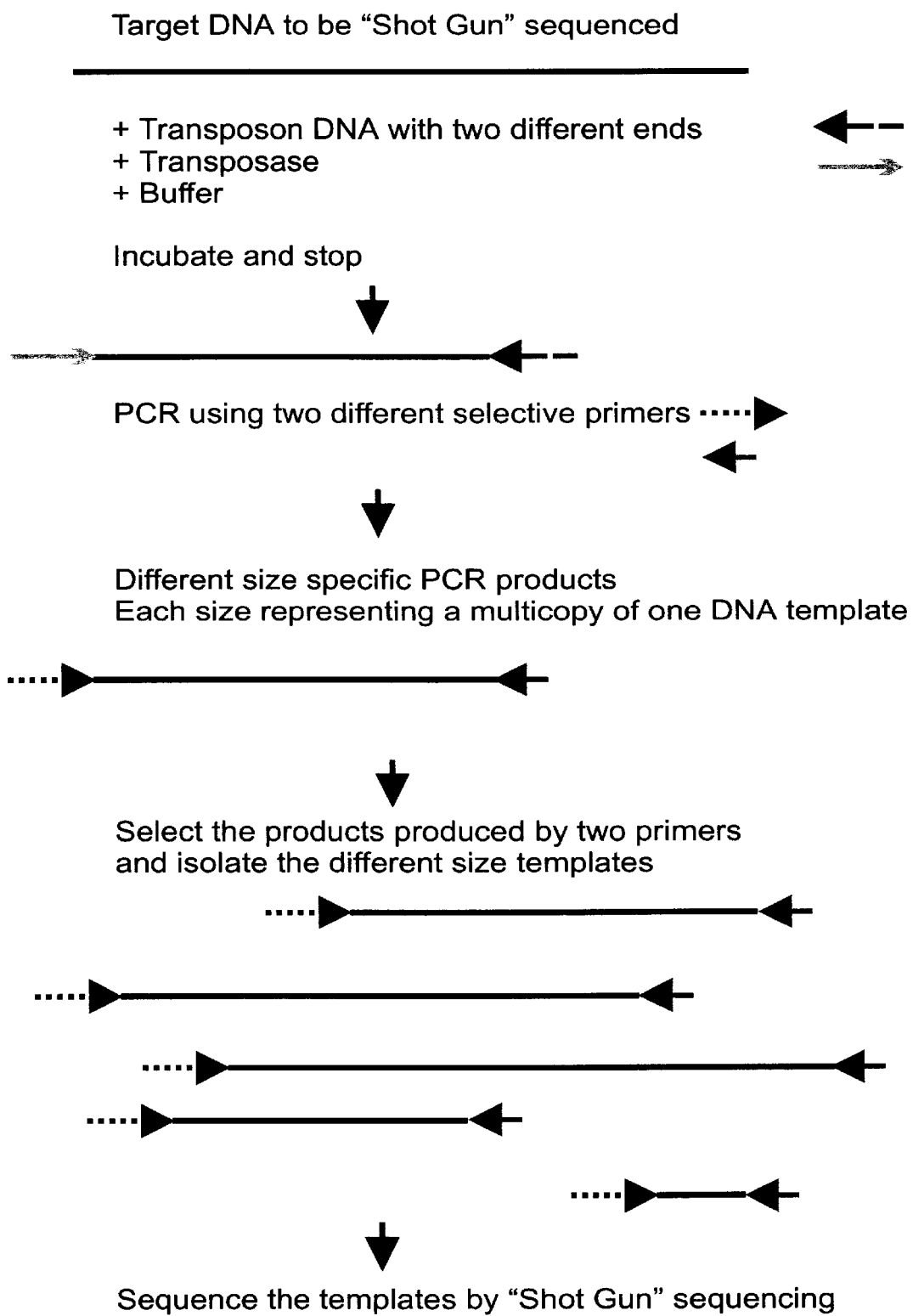
FIG. 2 is a schematic representation of the principle of a third embodiment (C) of the invention.

According to the third embodiment of this invention the method comprises the following steps (FIG. 2):

a) Two different sites for amplification primers are inserted to a target DNA by transposition. The transposition reaction is carried out by using transposons that have different ends enabling the design of different selective primers for both ends. The transposon ends can be parts of the same molecule or parts of two separate transposon molecules (Savilahti et al, 1995). In this embodiment it is preferable to have a more efficient transposition reaction than in the embodiments A and B in order to ensure a sufficient number of molecules having two transposon hits.

If required, the other DNA strand can be filled in by DNA polymerase and DNA ligase. Most of the transposition systems leave a nick or gap in one of the strands at their joining site to the target DNA.

b) A selective amplification reaction, such as a PCR reaction, is carried out by using two selective primers as amplification primers. One (first) primer is complementary to one (first) transposon end and the other (second) primer is complementary to the other (second) transposon end. In addition both selective primers have additional nucleotides of known identity at their 3' end.

The use of selective primers in the amplification reaction results in specific amplification products varying in size, each size representing one template for a sequencing reaction. An increasing amount of additional nucleotides improves the selection.

The selectivity can be accomplished by adding selective nucleotides into the end of only one of the primers. The selectivity can be still further improved by adding selective nucleotides at the end of both primers.

c) The amplification products are separated on the basis of their size by methods known in the art such as gel electrophoresis, capillary electrophoresis, HPLC or other well known methods.

Suitable templates for sequencing can be selected by exposing the amplification products to three parallel amplification reactions. In one of the reactions only one of the selective primers is used, in the other the second selective primer and in the third reaction both selective primers. Only those templates, which are the result of an amplification reaction by both primers are suitable templates for sequencing. However, a control PCR reaction with only one primer sometimes results in a product the same size as a product correctly produced by using both primers. Another method to select suitable templates is to use differently labeled primers and to test that both labels are present in the purified PCR product. The labels can be for example radioactive labels or fluorescent labels and the testing can be performed with an appropriate equipment depending on the labels.

d) The amplification products are situated at random positions at the target DNA. To be able to cover the whole sequence of the target DNA, a sufficient amount of specific amplification products are selected for sequencing templates.

The sequencing method can be any sequencing method known in the prior art like the nucleotide specific chemical reaction and cleavage reactions of Maxam and Gilbert (1977) and the primer extension reactions in the presence of nucleotide specific terminators as disclosed by Sanger et al (1977) preferably using cycle sequencing.

One of the advantages of the third embodiment (C) is that very long DNA segments can be sequenced by selecting the templates according to this embodiment. In this embodiment the present-day amplification reactions, such as PCR, are not a limiting factor, although more sequencing work is needed as compared to the first two embodiments (A and B). Another advantage is that no sequence data of the target DNA is needed nor any subcloning procedure is necessary.

One further object of the present invention is to provide a kit for selecting templates for DNA sequencing.

According to one embodiment of the invention the kit comprises:

a transposon comprising a DNA sequence which is recognizable by a transposase enzyme, said transposon DNA and said transposase enzyme being capable of forming a functional complex needed in a transposition reaction, a transposase enzyme for carrying out the transposition reaction, a fixed primer having a complementary sequence to the known sequence in the target DNA or if the target DNA is part of a vector, complementary to the known sequence in the vector adjacent to the insertion site of the target DNA, and a selective primer having a sequence complementary to the transposon joining end and having 1 to 10, preferably 1 to 5 additional nucleotides of known identity at its 3' end.

According to another embodiment of the invention the kit comprises:

a transposition complex comprising a transposon and a transposase enzyme, said transposon comprising a DNA sequence which is recognizable by said transposase enzyme, a fixed primer having a complementary sequence to the known sequence in the target DNA or if the target DNA is part of a vector, complementary to the known sequence in the vector adjacent to the insertion site of the target DNA, and a selective primer having a sequence complementary to the transposon joining end and having 1 to 10, preferably 1 to 5 additional nucleotides of known identity at its 3' end.

According to one further embodiment of the invention the kit comprises:

at least one transposon having two different joining ends comprising a DNA sequence or sequences which is/are recognizable by a transposase enzyme, said transposon and said transposase enzyme being capable of forming a functional complex needed in a transposition reaction;

a transposase enzyme for carrying out a transposition reaction, and a first selective primer, having a sequence complementary to the first joining end and having 0 to 10, preferably 0 to 5 additional nucleotides of known identity at its 3' end, and a second selective primer, said second primer having a sequence complementary to the second joining end and having 0 to 10, preferably 0 to 5 additional nucleotides of known identity at its 3' end, wherein at least one selective primer, said first or said second selective primer has 1 to 10, preferably 1 to 5 additional nucleotides at its 3' end.

The kit may also comprise other components needed in the transposition reaction. Such components may be other enzymes involved in the transposition reaction, or buffers, salts and/or stabilizers which have been chosen depending on the transposase/integrase system.

According to a preferred embodiment of this invention the transposon comprises the Mu transposon ends, recognizable by the MuA transposase.

The following non-limiting examples illustrate the invention in more detail.

EXAMPLE 1

Transposition Reaction

The target DNA is pUC19 plasmid (GeneBank access no. X02514). The transposition reaction has been carried out as essentially as described in Savilahti et al (1995) using a double stranded transposon DNA of the following sequence (SEQ ID NO:1):

5'TGAAGCGGCGCACGAAAAACGC-
GAAAGCGTTTCACGATAAATGCGAAAACAA
GCTTTTCCATCTCTCCTCCCCCCTG 3'

The 3' end of the complementary strand of the above sequence is joined to the target DNA in a transposition reaction.

The reaction conditions were the following:

10 nM Transposon DNA (donor DNA)
1.60 nM pUC19 DNA
15% DMSO
120 mM NaCl
0,05% Triton X-100
10 mM MgCl$_2$
25 mM Tris, pH 8.0
100 µg/ml BSA
15% Glycerol
8.7 µg/ml MuA
The reaction volume was 25 µl.

The reaction mixture was incubated at 30° C. for 1 h and frozen after the reaction.

Selective PCR Reaction

A selective PCR reaction was carried out by using primer 1 and 2 as the fixed PCR primers and primers 3, 4 or 5 as the selective PCR primers according to Table 2. The sequences of the primers are shown in Table 1.

TABLE 1

DNA sequences of the primers

| Primer number | Sequence | SEQ ID NO |
|---|---|---|
| 1 | AGCTGGCGAAAGGGGGATGTG | 2 |
| 2 | TTATGCTTCCGGCTCGTATGTTGTGT | 3 |
| 3 | GTTTTTCGTGCGCCGCTTCA | 4 |
| 4 | GTTTTTCGTGCGCCGCTTCAG | 5 |
| 5 | GTTTTTCGTGCGCCGCTTCAGA | 6 |
| 6 | GTTTTTCGTGCGCCGCTTCAGAG | 7 |
| 7 | GTTTTTCGTGCGCCGCTTCAGAGT | 8 |
| 8 | GTTTTTCGTGCGCCGCTTCAGATCT | 9 |
| 9 | CGGCGGGAGTTTGGGAGGTT | 10 |
| 10 | GCGGCGGGAGTTTGGGAG | 11 |
| 11 | CGCTTTCGTACTTCAAGTGAATCAATACA | 12 |
| 12 | CGCTTTCGTACTTCAAGTGAATCAATACAG | 13 |
| 13 | CGCTTTCGTACTTCAAGTGAATCAATACAGA | 14 |
| 14 | CGCTTTCGTACTTCAAGTGAATCAATACAGAG | 15 |
| 15 | CGCTTTCGTACTTCAAGTGAATCAATACAGAGT | 16 | wherein 1 is a fixed primer in forward direction of pUC19

2 is a fixed primer in reverse direction of pUC19

3 to 8 are selective primers with 0 to 5 selective nucleotides complementary to donor A 9 and 10 are primers complementary to donor B adjacent to the nonjoining end 11 to 15 are selective primers with 0 to 4 selective nucleotides complementary to donor B

TABLE 2

| Reaction number | Fixed primer according to Table 1 | Selective primer according to Table 1 |
|---|---|---|
| 1 | 1 | 3 |
| 2 | 1 | 4 |
| 3 | 1 | 5 |
| 4 | 2 | 3 |
| 5 | 2 | 4 |
| 6 | 2 | 5 |

The PCR reaction conditions were the following:

1 µl of ten-fold diluted transposition reaction mixture 0.4 µM of each primer 1 or 2 and primer 3, 4 or 5 according to Table 2

200 µM dNTP (per each nucleotide)

1.5 mM MgCl$_2$ 10 mM Tris-HCl pH 8.3

50 mM KCl

2U Dynazyme II DNA polymerase (F-501, Finnzymes Oy, Finland)

The reaction volume was 50 µl. Prior to adding the primers the reaction mixture was incubated 10 min at 72° C. to fill in the gap at the insertion site between the 3' end of the target DNA and the 5' end of the transposon DNA.

Cycling conditions:

| Step | Time | T |
|---|---|---|
| 1 | 1 min 30 s | 96° C. |
| 2 | 45 s | 96° C. |
| 3 | 2 min | 72° C. |

-continued

| Step | Time | T |
|---|---|---|
| 4 | 29 times to step 2 | |
| 5 | 5 min | 72° C. |
| 6 | kept until removed | 4° C. |

The PCR equipment was a DNA Engine from MJ-Research, Massachusetts, USA.

PCR reactions were loaded and run on regular 1,8% agarose gel. The result is shown in FIG. 4.

Using an 18 G needle small samples of fragments from reactions 3 and 6 from the gel were transformed into new PCR reactions and PCR was performed using the same primers and conditions as in the previous PCR reaction. In addition, a control PCR using only the selective primer was done (see FIG. 5, reaction B). The new PCR reactions were loaded and run on 1.8% agarose gel resulting in separate DNA fragments of different sizes. Primers and nucleotides were removed from each reaction using an AGTC purification system according to the manufacturer's instructions (Advanced Genetic Technologies Corporation, Maryland, USA). Purified DNA fragments served as sequencing templates (FIG. 5).

The sequencing was done using Thermo Sequenace cycle sequencing kit according to the manufacturer's instructions using $P^{33}$ labeled primers (Amersham Life Science, UK). The sequencing reactions were run on a 6% Gene Page Plus polyacrylamide gel (Amresco, Ohio, USA) using a single loading.

TABLE 3

| Fragment # | Reaction # | Size | Sequence location at pUC19 | Sequence length read |
|---|---|---|---|---|
| 1 | 3 | 162 bp | 318 to 469 | 151 |
| 2 | 3 | 374 bp | 457 to 681 | 224 |
| 3 | 3 | 646 bp | 670 to 953 | 283 |
| 4 | 4 | 347 bp | 188 to 325 | 137 |
| 5 | 5 | 503 bp | 32 to 202 | 170 |

It was possible to sequence 921 bp of pUC19 in one run. The pUC19 was chosen as target DNA because the sequence was known. The experiment shows that the method works and could be employed to select templates for sequencing longer DNA segments. The only limiting factor is the capacity of the PCR reaction to produce longer DNA fragments.

EXAMPLE 2

The target DNA to be sequenced is the 6557 bp DNA fragment from Lambda DNA-HindIII digestion inserted into pUC19 at the HindIII site.

The transposition reaction was carried out as described in Savilahti et al (1995) using a double stranded transposon DNA (donor A) of the following sequence (SEQ ID NO:1):

5'TGAAGCGGCGCACGAAAAACGC-
GAAAGCGTTTCACGATAAATGCGAAAACAA
GCTTTTCCATCTCTCCTCCCCCCTG3'

The 3' end of the complementary strand of the above sequence is joined to the target DNA in a transposition reaction.

The reaction conditions were the following:
50 nM Transposon DNA (donor A)
1.6 nM (10 ng/µl) pUC19 DNA having 6557 bp insert from lambda phage
15% DMSO
120 mM NaCl
0.05% Triton X-100
10 mM $MgCl_2$
25 mM Tris, pH 8.0
100 µg/ml BSA
15% Glycerol
8.7 µg/ml MuA The reaction volume was 50 µl.

The reaction mixture was incubated at 30° C. for 1 h and frozen after the reaction.

Selective PCR Reaction

Two different selective PCR reactions were carried out by using forward primer 1 (reaction A) or reverse primer 2 (reaction B) as the fixed PCR primer and primer 7 as the selective primer. The sequences of the primers are shown in Table 1 in Example 1.

The PCR reaction conditions were the following:
1 µl of ten-fold diluted transposition reaction mixture
0.4 µM of primer 1 (reaction A) or primer 2 (reaction B)
0.4 µM primer 7
360 µM dNTP (per each nucleotide)
1.8 mM $MgCl_2$
50 mM Tris-HCl (pH 9.0 at 25° C.)
15 mM $(NH_4)_2SO_4$
0.1% Triton X-100
1 U Dynazyme EXT DNA polymerase (F-501, Finnzymes Oy, Finland)
$H_2O$ added to 50 µl Cycling conditions for reaction A:

| Step | Time | T |
|---|---|---|
| 1 | 1 min 30 s | 96° C. |
| 2 | 45 s | 96° C. |
| 3 | 8 min | 72° C. |
| 4 | 29 times to step 2 | |
| 5 | 8 min | 72° C. |
| 6 | kept until removed | 4° C. |

Cycling conditions for reaction B:

| Step | Time | T |
|---|---|---|
| 1 | 1 min 30 s | 96° C. |
| 2 | 45 s | 96° C. |
| 3 | 1 min | 68° C. |
| 4 | 5 min | 72° C. |
| 5 | 29 times to step 2 | |
| 6 | 10 min | 72° C. |
| 7 | kept until removed | 4° C. |

The PCR instrument was a PTC-200 DNA Engine from MJ-Research, Massachusetts, USA.

PCR reactions were loaded and run on 1% Seakem LE agarose gel (FMC) in TBE buffer. The gel was stained after the run with 1:10,000 diluted SYBR Green gel stain (FMC) for 30 minutes in a low speed shaker at room temperature. SYBR Green gel stain is more sensitive than ethidium bromide and facilitates sampling of especially large lower intensity PCR products from the gel. The results are shown in FIG. 6.

Using a 10 μl disposable pipette tip samples of specific fragments from reactions A (17 fragments) and B (16 fragments) were picked from the gel and transferred into 20 μl TE buffer. One micro liter of samples were then used in new PCR reactions. PCR was performed using the same primers and conditions as in the previous PCR reaction except that the extension time of A samples was shortened from 8 minutes to 5 minutes at 72° C. In addition, a control PCR using only the selective primer or fixed primer was done for B samples. The new PCR reactions were loaded and run on 1.0% agarose gel resulting in separate DNA fragments of different sizes. Results are shown in FIG. 7.

Reactions A3, A4, A5, A8, B5–B16 had several fragments in the same reaction. The desired fragments were isolated and purified from the gel using Qiaex II Gel Extraction Kit (Qiagen, USA) according to manufacturer's instructions.

Reactions A6, A9, A12, A13, A14, A15, A16 and A17 showed only one main band and they were purified directly by Qiaquick PCR purification kit (Qiagen, USA) according to the manufacturer's instructions.

The purified DNA templates were sequenced by using SequiTherm EXCEL II Long-Read DNA Sequencing Kit (Epicentre Technologies, USA) according to their Cycle Sequencing Protocol for Li-Cor automated DNA sequencer. The used amount of each DNA template was 7.8 μl. The sequencing primer was IRD800 labeled primer 3 (Table 1).

The cycling parameters were:

| Step | time | temperature |
|---|---|---|
| 1 | 5 min | 95° C. |
| 2 | 30 sec | 95° C. |
| 3 | 15 sec | 67° C. |
| 4 | 1 min | 70° C. |
| 5 | 29 times to step 2 | |
| 6 | kept until removed | 4° C. |

The automated DNA sequencing apparatus was a Li-Cor Long Read IR 4200. The used gel length was 66 cm and the gel was 4% Long Ranger (FMC).

The sequencing data were assembled with Lasergene Seqman software (Dnastar, Wis., USA). Data are shown in FIG. 8.

Of the 33 selected fragments 17 sequencing templates were received and sequenced. With received sequence data it was possible to cover the full sequence of the 6557 bp insert of lambda phage. The insert is in the vector at the position from 450 to 7007. The accuracy of the sequence from position 450 to 4200 was better than 99% and the accuracy of the sequence from 4970 to 7050 was better than 98% compared to the known sequence of lambda DNA.

This example shows that according to the method of this invention it is possible to rapidly sequence in vitro a larger DNA insert in a vector. To get more complete sequence it is preferable to use several different selective primers to produce more templates to be sequenced.

EXAMPLE 3

Transposition Reaction

The target DNA was pUC19 plasmid.

The transposition reaction was carried out essentially as described in Savilahti et al (1995) using a mixture of two different double stranded transposon DNAs (donor A and donor B) of the following sequences (SEQ ID NO:1 and SEQ ID NO:17) capable of forming a functional transposon complex with MuA transposase:

Donor A (SEQ ID NO:1)
5' TGAAGCGGCGCACGAAAAACGC-
GAAAGCGTTTCACGATAAATGCGAAAA-
CAAGCTTTTCCATCT CTCCTCCCCCTG 3'

Donor B (SEQ ID NO:17)
5'GTATTGATTCACTTGAAGTAC-
GAAAGCGTTTCACGAAAAACGCGAAAG-
CAGATCTAACCTCCC CTCCCGCCGC 3'

The 3' end of the complementary strand of the above sequences is joined to the target DNA in a transposition reaction.

The reaction conditions were the following:

250 nM Transposon DNA (donor A DNA) SEQ ID NO:1

250 nM Transposon DNA (donor B DNA) SEQ ID NO:17

5.7 nM (10 ng/μl) pUC19

15% DMSO 120 mM NaCl 0.05% Triton X-100

10 mM MgCl$_2$ 25 mM Tris, pH 8.0

100 μg/ml BSA

15% Glycerol

87 μg/ml MuA

H$_2$O added to 50 μl

The reaction mixture was incubated at 30° C. for 4 h. 10 μl of MuA stop solution, 2.5% SDS, 25% Ficoll 400, 0.025% bromophenol blue and 50 mM EDTA were added to the reaction. 10 μl samples of the reaction were loaded in to 5 lanes on a 0.8% Seaplaque agarose gel (FMC) and run on a standard horizontal gel apparatus in TAE buffer.

The first transposon hit to the circular pUC19 plasmid causes the linearization of the plasmid. Two or more transposon hits to the same plasmid molecule result in different random size products that are seen on the FIG. 9 as a smear under the linearized plasmid DNA. That DNA was isolated by cutting off that part of the gel and solubilized and extracted twice with an equal volume of phenol solution and once with an equal volume of chloroform/isoamylalcohol (24:1). Sodium acetate was added to 300 mM final concentration and DNA was precipitated by adding two volumes of ethanol. After drying the DNA was dissolved in 120 μl of TE buffer (10 mM Tris, 0.1 mM EDTA, pH 8.0).

Selective PCR Reaction

Selective PCR was done in two steps. In the first step the PCR was done using primer 3 or primer 4 and primer 9 or 10 according to the Table 1 and 4. Primer 3 and 4 are complementary to the joining end of donor A having 0 or 1 selective nucleotide. Primer 9 and 10 are complementary to the non joining end of donor B having no selective nucleotides. Control reactions having only one primer were also done.

The PCR reaction conditions were the following:

1 μl of gel isolated transposition reaction mixture 0.4 μM of each primer according to Table 4

200 μM dNTP (per each nucleotide)

1.5 mM MgCl$_2$ 10 mM Tris-HCl pH 8.3

50 mM KCl 0.01% (w/V) gelatin 2.5 U AmpliTaq Gold DNA polymerase (Perking Elmer, USA)

H₂O added to 50 μl
PCR Cycling conditions:

| Step | Time | T |
| --- | --- | --- |
| 1 | 9 min | 95° C. |
| 2 | 1 min 30 s | 96° C. |
| 3 | 45 s | 96° C. |
| 4 | 1 min | 68° C. |
| 5 | 2 min | 72° C. |
| 6 | 29 times to step 3 | |
| 7 | 5 min | 72° C. |
| 8 | kept until removed | 4° C. |

TABLE 4

| Reaction number | Donor A primer according to Table 1 | Donor B primer according to Table 1 |
| --- | --- | --- |
| 1 | 3 | 9 |
| 2 | No primer | 9 |
| 3 | 3 | 10 |
| 4 | No primer | 10 |
| 5 | 3 | No primer |
| 6 | 4 | 9 |
| 7 | 4 | 10 |
| 8 | 4 | No primer |

The PCR instrument was a PTC-200 DNA Engine from MJ-Research, Massachusetts, USA. 9 μl of each reaction were run on regular 2% agarose gel electrophoresis stained with ethidium bromide. The results are shown in FIG. 10.

The PCR reaction number 6 showed a good distribution of different size PCR products. Reaction 6 was used in the second step PCR. The aim was to study what selection strength is needed.

Selective primers were now used at both sides (Donor A and Donor B) according to Table 5. The PCR conditions and cycles and the electrophoresis of the samples were the same as in the previous PCR. The results are shown in FIG. 11.

TABLE 5

| Reaction number | Primer A | Primer B | Selective nucleotides at Donor A side | Selective nucleotides at Donor B side |
| --- | --- | --- | --- | --- |
| 1 | 5 | 11 | GA | — |
| 2 | no primer | 11 | — | — |
| 3 | 5 | 12 | GA | G |
| 4 | no primer | 12 | — | G |
| 5 | 5 | 13 | GA | GA |
| 6 | no primer | 13 | — | GA |
| 7 | 5 | 14 | GA | GAG |
| 8 | no primer | 14 | — | GAG |
| 9 | 5 | 15 | GA | GAGT |
| 10 | no primer | 15 | — | GAGT |
| 11 | 5 | no primer | GA | — |
| 12 | 6 | 11 | GAG | — |
| 13 | 6 | 12 | GAG | G |
| 14 | 6 | 13 | GAG | GA |
| 15 | 6 | 14 | GAG | GAG |
| 16 | 6 | 15 | GAG | GAGT |
| 17 | 6 | no primer | GAG | — |
| 18 | 7 | 11 | GAGT | — |
| 19 | 7 | 12 | GAGT | G |
| 20 | 7 | 13 | GAGT | GA |
| 21 | 7 | 14 | GAGT | GAG |
| 22 | 7 | 15 | GAGT | GAGT |
| 23 | 7 | no primer | GAGT | — |
| 24 | 8 | 11 | GATCT | — |
| 25 | 8 | 12 | GATCT | G |
| 26 | 8 | 13 | GATCT | GA |
| 27 | 8 | 14 | GATCT | GAG |
| 28 | 8 | 15 | GATCT | GAGT |
| 29 | 8 | no primer | GATCT | — |

Different selections in the PCR resulted in different specific DNA bands on agarose gel electrophoresis. Control reactions with only one primer showed that some of the PCR products have Donor A at both ends.

Selection of reactions 12, 13, 14, 17, 18, 19, 20, 23, 24, 25, 26 and 29 were run again on a 4% Metaphor agarose (FMC) electrophoresis in TBE-buffer. The gel was stained after the run with 1:10,000 diluted SYBR Green gel stain (FMC) for 30 minutes in a low speed shaker at room temperature. The results are shown in the FIG. 12.

Using 10 μl disposable pipette tips 15 samples of different specific fragments were picked and transferred into 20 μl TE buffer. Those samples were then used as a template in the next PCR to amplify the specific products.

The PCR reaction conditions were the following:

1 μl of template
0.4 μM of each primer according to Table 6
200 μM dNTP (per each nucleotide)
1.5 mM MgCl₂
10 mM Tris-HCl pH 8.3
50 mM KCl
1 U Dynazyme II DNA polymerase (F-501, Finnzymes Oy, Finland)
H₂O added to 50 μl

TABLE 6

| Reaction number | Primer A | Primer B |
| --- | --- | --- |
| 1 | 6 | 11 |
| 2 | 6 | 11 |
| 3 | 6 | 11 |
| 4 | 6 | 11 |
| 5 | 7 | 11 |
| 6 | 7 | 11 |
| 7 | 7 | 11 |
| 8 | 7 | 11 |
| 9 | 7 | 11 |
| 10 | 8 | 11 |
| 11 | 8 | 11 |
| 12 | 8 | 11 |
| 13 | 8 | 11 |
| 14 | 8 | 11 |
| 15 | 8 | 11 |

Cycling conditions for reactions

| Step | Time | T |
| --- | --- | --- |
| 1 | 1 min 30 s | 96° C. |
| 2 | 45 s | 96° C. |
| 3 | 1 min | 68° C. |
| 4 | 2 min | 72° C. |
| 5 | 29 times to step 2 | |
| 6 | 5 min | 72° C. |
| 7 | kept until removed | 4° C. |

5 μl samples of the reactions were run on a 2% standard agarose gel electrophoresis stained with ethidium bromide.

The results are shown in FIG. 13. Reactions 6, 7, 8, 10, 13 and 15 showed only one main fragment and were purified by Qiaquick PCR purification kit (Qiagen, USA) according to the manufacturer's instructions. Two fragments from reaction 4 and one fragment from each of reactions 9 and 14 were isolated and purified from the gel using Qiaex II Gel Extraction Kit (Qiagen, USA) according to the manufacture's instructions.

Cycle Sequencing of the isolated DNA templates

The purified DNA templates were sequenced by using the Thermo Sequenase cycle sequencing kit according to the manufacturer's instructions using IRD800 labeled primer 3 (Table 1).

The cycling parameters were:

| Step | time | temperature |
|---|---|---|
| 1 | 30 sec | 95° C. |
| 2 | 30 sec | 67° C. |
| 3 | 1 min 30 sec | 72° C. |
| 4 | 60 times to step 2 | |
| 5 | kept until removed | 4° C. |

The automated DNA sequencing apparatus was a Li-Cor Long Read IR 4200. The used gel length was 41 cm and the gel was 6% Gene Page (Amresco, USA).

The sequencing data were assembled with Lasergene Seqman software (Dnastar, Wis., USA) and compared to the known sequence of the pUC19 plasmid. Data are shown in FIG. 14.

The experiment shows that the method works and could be employed to select templates for sequencing of an unknown DNA without any subcloning and completely in vitro.

References

Ausubel, F. M., Brent, R., Kingston, R. E., Moore, D. D., Seidman, J. G., Smith, J. A. and Struhl, K., 1989, Current Protocols in Molecular Biology 1.

Boeke J. D. 1989. Transposable elements in Saccharomyces cerevisiae in Mobile DNA. Berg D. E. and Howe M. M. eds. American society for microbiology, Washington D. C. pp. 335–374.

Craig N. L. 1995. Unity in transposition reactions. Science 270: 253–254.

Craig N. L. 1996. Transposon Tn7. Curr. Top. Microbiol. Immunol. 204: 27–48.

De Noronha, Carlos M. C. and Mullins, James I., PCR Methods Appl. ,1992, 2(2): 131–6.

Devine, S. E. and Boeke, J. D., Nucleic Acids Research, 1994, 22(18): 3765–3772.

Ichikawa H. and Ohtsubo E., J. Biol. Chem., 1990, 265(31): 18829–32.

Itakura, K., Rossi, J. J. and Wallace, R. B., Ann. Rev. Biochem. 1984, 53: 323–356.

Kasai, H. Isono, S., Kitakawa, M., Mineno, J., Akiyama, H., Kurnit, D. M., Berg, D. E. and Isono, K. Nucleis Acids Research, 1992, 20 (24): 6509–6515.

Kaufman P. and Rio D. C., Cell, 1992, 69(1): 27–39.

Kleckner N., Chalmers R. M., Kwon D., Sakai J. and Bolland S. Tn10 and IS10 Transposition and chromosome rearrangements: mechanism and regulation in vivo and in vitro. Curr. Top. Microbiol. Immunol., 1996, 204: 49–82.

Krishnan, R. et al., Methods in Enzymology. Transposon-based and polymerase chain treacion-based sequencing of DNAs cloned in a phage, 1993, Vol. 218.

Lampe D. J., Churchill M. E. A. and Robertson H. M., EMBO J.,1996, 15(19): 5470–5479.

Liang P. and Pardee B., Science, 1992, 257: 967–971.

Maxam and Gilbert, PNAS, 1977, 74:560.

Ohtsubo E. & Sekine Y. Bacterial insertion sequences. Curr. Top. Microbiol. Immunol., 1996,204: 1–26.

Park B. T., Jeong M. H. and Kim B. H., Taehan Misaengmul Hakhoechi, 1992, 27(4): 381–9.

Roach, J. L., Boysen, C., Wang, K. and Hood, L., 1995, 26(2):345–53.

Sambrook, J., Fritch, E. F. and Maniatis, T., 1989. Molecular Cloning A Laboratory Manual, Second Edition, Cold Spring Harbor Laboratory Press, Cold Spring Harbor, N.Y.

Sanger, F., Nicklen, S., and Coulson, A. R., Proc. Natl. Acad. Sci. USA, 1977, 74: 5463–5467.

Savilahti, H., Rice, P. A. and Mizuuchi, K., The EMBO Journal, 1995, 14(19): 4893–4903.

Strathmann M., Hamilton B. A., Mayeda C. A., Simon M. I., Meyerowitz E. M. and Palazzolo M. J., Proc. Natl. Acad. Sci. USA, 1991, 88:1247–1250.

Sulston, J., Du, Z., Thomas, K., Wilson, R., Hillier, L., Staden, R., Nature 1992, 356: 37–41.

Varmus H and Brown. P. A. 1989. Retroviruses. in Mobile DNA. Berg D. E. and Howe M. M. eds. American society for microbiology, Washington D.C. pp.53–108.

Vos J. C., Baere I. And Plasterk R. H. A., Genes Dev., 1996,10(6): 755–61.

What is claimed is:

1. An in vitro method for providing templates for DNA sequencing, comprising the steps of
   carrying out a transposition reaction in the presence of a target DNA and in the presence of a transposon, said transposition reaction resulting in at least one insertion into said target DNA;
   performing an amplification reaction by using as primers a first, fixed primer hybridizing at a known location in said target DNA or, if the target DNA is part of a vector, adjacent to said target DNA, and a second, selective primer hybridizing at the transposon insertion site, said selective primer having a sequence complementary to the joining end of said transposon and having additional nucleotides of known identity at its 3' end;
   separating the amplification products on the basis of their size, and
   recovering said amplification products suitable for use as templates in sequencing said target DNA.

2. The method according to claim 1, wherein the amplification products useful as templates overlap each other and differ in size from each other.

3. The method according to claim 1, wherein the first, fixed primer and the second, selective primer are differently labeled by labels such as radioactive labels or fluorescence labels and from the amplification products are selected for use as templates in sequencing those which have both labels.

4. The method according to claim 1, wherein said amplification reaction is a PCR reaction.

5. The method according to claim 1, wherein said target DNA is a circular DNA or part of a circular DNA.

6. The method according to claim 1, wherein said target DNA is a linear DNA or part of a linear DNA.

7. The method according to claim 1, wherein said target DNA is inserted into a vector and said first, fixed primer, has a sequence complementary to the vector sequence adjacent to the target insertion site.

8. The method according to claim 1, wherein the transposon comprises a DNA sequence which is recognizable by a transposase enzyme, and said transposon DNA and said transposase enzyme form a functional complex needed in the transposition reaction.

9. The method according to claim 1, wherein the transposon comprises the Mu transposition ends, recognizable by the MuA transposase.

10. An in vitro method for providing templates for DNA sequencing, comprising the steps of:

carrying out a transposition reaction in the presence of at least one transposon having two different joining ends, said joining ends differing from each other by at least one nucleotide;

performing an amplification reaction by using as primers a first, selective primer, having a sequence complementary to the first joining end and a second, selective primer, said second primer having a sequence complementary to the second joining end wherein at least said first or said second selective primer has additional nucleotides of known identity at its 3' end;

separating said amplification products on the basis of their size;

selecting templates for DNA sequencing among the amplification products which have different ends and which are produced only by both primers together, and recovering said amplification products suitable for use as templates in sequencing said target DNA.

11. The method according to claim 10, wherein the first primer and the second primer are differently labeled by labels such as radioactive labels or fluorescence labels and from the amplification products are selected for use as templates in sequencing those which have both labels.

12. The method according to claim 11, wherein the amplification reaction is a PCR reaction.

13. The method according to claim 10, wherein the transposon or transposons is/are recognizable by a transposase enzyme, and said transposon DNA and said transposase enzyme form a functional complex needed in the transposition reaction.

14. The method according to claim 10, wherein the transposon comprises the Mu transposon ends, recognizable by the MuA transposase.

* * * * *

SEQUENCE LISTING

<160> NUMBER OF SEQ ID NOS: 17

<210> SEQ ID NO 1
<211> LENGTH: 77
<212> TYPE: DNA
<213> ORGANISM: Artificial Sequence
<220> FEATURE:
<223> OTHER INFORMATION: Derived from phage Mu from E. coli

<400> SEQUENCE: 1
tgaagcggcg cacgaaaaac gcgaaagcgt ttcacgataa atgcgaaaac aagcttttcc    60
atctctcctc cccctg              77

<210> SEQ ID NO 2
<211> LENGTH: 21
<212> TYPE: DNA
<213> ORGANISM: Artificial Sequence
<220> FEATURE:
<223> OTHER INFORMATION: Primer No. 1. Derived from pUC19 from E. coli

<400> SEQUENCE: 2
agctggcgaa aggggatgt g              21

<210> SEQ ID NO 3
<211> LENGTH: 26
<212> TYPE: DNA
<213> ORGANISM: Artificial Sequence
<220> FEATURE:
<223> OTHER INFORMATION: Primer No. 2. Derived from pUC19 from E. coli

<400> SEQUENCE: 3
ttatgcttcc ggctcgtatg ttgtgt              26

<210> SEQ ID NO 4
<211> LENGTH: 20
<212> TYPE: DNA
<213> ORGANISM: Artificial Sequence
<220> FEATURE:
<223> OTHER INFORMATION: Primer No. 3. Derived from phage Mu from
      E. coli

<400> SEQUENCE: 4 gttttcgtg cgccgcttca              20

<210> SEQ ID NO 5
<211> LENGTH: 21
<212> TYPE: DNA
<213> ORGANISM: Artificial Sequence
<220> FEATURE:
<223> OTHER INFORMATION: Primer No. 4. Derived from phage Mu from
      E. coli

<400> SEQUENCE: 5 gttttcgtg cgccgcttca g              21

<210> SEQ ID NO 6
<211> LENGTH: 22
<212> TYPE: DNA
<213> ORGANISM: Artificial Sequence
<220> FEATURE:
<223> OTHER INFORMATION: Primer No. 5. Derived from phage Mu from
      E. coli

<400> SEQUENCE: 6 gttttcgtg cgccgcttca ga              22

<210> SEQ ID NO 7
<211> LENGTH: 23
<212> TYPE: DNA
<213> ORGANISM: Artificial Sequence
<220> FEATURE:
<223> OTHER INFORMATION: Primer No. 6. Derived from phage Mu from
      E. coli

<400> SEQUENCE: 7 gttttcgtg cgccgcttca gag              23

<210> SEQ ID NO 8
<211> LENGTH: 24
<212> TYPE: DNA
<213> ORGANISM: Artificial Sequence
<220> FEATURE:
<223> OTHER INFORMATION: Primer No. 7.  Derived from phage Mu from
      E. coli

<400> SEQUENCE: 8
gtttttcgtg cgccgcttca gagt                                          24

<210> SEQ ID NO 9
<211> LENGTH: 25
<212> TYPE: DNA
<213> ORGANISM: Artificial Sequence
<220> FEATURE:
<223> OTHER INFORMATION: Primer No. 8.  Derived from phage Mu from
      E. coli

<400> SEQUENCE: 9
gtttttcgtg cgccgcttca gatct                                         25

<210> SEQ ID NO 10
<211> LENGTH: 20
<212> TYPE: DNA
<213> ORGANISM: Artificial Sequence
<220> FEATURE:
<223> OTHER INFORMATION: Primer No. 9.  Derived from phage Mu from
      E. coli

<400> SEQUENCE: 10
cggcgggagt ttgggaggtt                                               20

<210> SEQ ID NO 11
<211> LENGTH: 18
<212> TYPE: DNA
<213> ORGANISM: Artificial Sequence
<220> FEATURE:
<223> OTHER INFORMATION: Primer No. 10.  Derived from phage Mu from
      E. coli

<400> SEQUENCE: 11
gcggcgggag tttgggag                                                 18

<210> SEQ ID NO 12
<211> LENGTH: 29
<212> TYPE: DNA
<213> ORGANISM: Artificial Sequence
<220> FEATURE:
<223> OTHER INFORMATION: Primer No. 11.  Derived from phage Mu from
      E. coli

<400> SEQUENCE: 12
cgctttcgta cttcaagtga atcaataca                                     29

<210> SEQ ID NO 13
<211> LENGTH: 30
<212> TYPE: DNA
<213> ORGANISM: Artificial Sequence
<220> FEATURE:
<223> OTHER INFORMATION: Primer No. 12.  Derived from phage Mu from
      E. coli

<400> SEQUENCE: 13
cgctttcgta cttcaagtga atcaatacag                                    30

<210> SEQ ID NO 14

-continued

```
<211> LENGTH: 31
<212> TYPE: DNA
<213> ORGANISM: Artificial Sequence
<220> FEATURE:
<223> OTHER INFORMATION: Primer No. 13.  Derived from phage Mu from
      E. coli

<400> SEQUENCE: 14
cgctttcgta cttcaagtga atcaatacag a                              31

<210> SEQ ID NO 15
<211> LENGTH: 32
<212> TYPE: DNA
<213> ORGANISM: Artificial Sequence
<220> FEATURE:
<223> OTHER INFORMATION: Primer No. 14.  Derived from phage Mu from
      E. coli

<400> SEQUENCE: 15
cgctttcgta cttcaagtga atcaatacag ag                             32

<210> SEQ ID NO 16
<211> LENGTH: 33
<212> TYPE: DNA
<213> ORGANISM: Artificial Sequence
<220> FEATURE:
<223> OTHER INFORMATION: Primer No. 15.  Derived from phage Mu from
      E. coli

<400> SEQUENCE: 16
cgctttcgta cttcaagtga atcaatacag agt                            33

<210> SEQ ID NO 17
<211> LENGTH: 77
<212> TYPE: DNA
<213> ORGANISM: Artificial Sequence
<220> FEATURE:
<223> OTHER INFORMATION: Derived from phage Mu from E. coli

<400> SEQUENCE: 17
tgtattgatt cacttgaagt acgaaagcgt ttcacgaaaa acgcgaaagc agatctaacc    60
tcccaaactc ccgccgc                                                  77
```